US006176904B1

(12) United States Patent
Gupta

(10) Patent No.: US 6,176,904 B1
(45) Date of Patent: Jan. 23, 2001

(54) BLOOD FILTER

(76) Inventor: Brij M. Gupta, 21631 Bogarra, Mission Viejo, CA (US) 92692

( * ) Notice: Under 35 U.S.C. 154(b), the term of this patent shall be extended for 0 days.

(21) Appl. No.: 09/346,896

(22) Filed: Jul. 2, 1999

(51) Int. Cl.[7] .................................................. B01D 19/00
(52) U.S. Cl. ................. 96/209; 96/216; 96/219; 96/212; 96/220; 210/188; 210/436; 210/304
(58) Field of Search .............. 96/204, 206, 208, 96/209, 212, 216, 219, 220; 95/260, 261, 262; 210/188, 436, 446, 453, 455, 472, 497.01, 497.1, 304; 604/4

(56) References Cited

U.S. PATENT DOCUMENTS

| Re. 32,711 | * | 7/1988 | Dickens et al. ....................... 210/436 |
| 4,203,961 | * | 5/1980 | Cowley ................................... 96/209 |
| 4,276,171 | * | 6/1981 | Jackson ........................... 210/497.01 |
| 4,344,777 | * | 8/1982 | Siposs .................................... 96/206 |
| 4,411,783 | * | 10/1983 | Dickens et al. ....................... 210/436 |
| 4,743,371 | * | 5/1988 | Servas et al. ........................... 210/98 |
| 4,806,135 | * | 2/1989 | Siposs .................................... 96/212 |
| 4,919,802 | * | 4/1990 | Katsura ................................. 210/188 |
| 4,932,987 | * | 6/1990 | Molina .................................... 96/212 |
| 4,964,984 | * | 10/1990 | Reeder et al. ....................... 210/188 |
| 5,252,229 | * | 10/1993 | Rojey et al. ......................... 210/787 |
| 5,258,127 | * | 11/1993 | Gsell et al. .......................... 210/188 |
| 5,312,479 | * | 5/1994 | Weinstein et al. .................. 210/188 |
| 5,334,239 | * | 8/1994 | Choe et al. ............................ 95/261 |
| 5,372,718 | * | 12/1994 | Zebian ................................. 210/436 |
| 5,484,474 | * | 1/1996 | Weinstein et al. ..................... 96/209 |
| 5,618,425 | * | 4/1997 | Mitamura et al. .................. 210/436 |
| 5,632,894 | * | 5/1997 | White et al. ......................... 210/436 |
| 5,649,998 | * | 7/1997 | Ungerer et al. ........................ 96/209 |
| 5,651,765 | * | 7/1997 | Haworth et al. ..................... 210/188 |
| 5,782,791 | * | 7/1998 | Peterson et al. .................... 604/4.01 |
| 5,849,065 | * | 12/1998 | Woike ................................... 96/209 |

* cited by examiner

*Primary Examiner*—Duane Smith
*Assistant Examiner*—Jason M. Greene
(74) *Attorney, Agent, or Firm*—Roger C. Turner

(57) ABSTRACT

An arterial blood filter device for removing foreign particles and undissolved gases from blood flowing through the device, having a cylindrical housing enclosing a cylindrical filter element between a hollow upper cap forming an inlet chamber and a flat lower cap forming an outlet chamber. The upper cap has a vertical gas outlet and has a horizontal tubular inlet with the outermost wall of the tubular inlet extending tangentially from the outermost wall of the base of the upper cap. A principle feature of the invention is a stepped dome having a circular base with a diameter closely matched to the outer diameter of the filter element and attached to the upper end thereof. The stepped dome includes hemispherically shaped upper surface extending into the inlet chamber and having a maximum diameter smaller than the diameter of the circular base. The center of the upper surface of the stepped dome is offset from the central axis in a direction away from the tubular blood inlet so that the dome does not obstruct the path of blood into and around the inlet chamber. The stepped dome further includes a thin elevated ridge that extends from the base in an upward spiraling manner through about one revolution to the top of the upper surface of the dome to facilitate the removal of undissolved gases and to facilitate the flow of blood flow through the inlet chamber of the device.

15 Claims, 4 Drawing Sheets

BLOOD FILTER

BACKGROUND OF THE INVENTION

The present invention relates to blood filters that are used in extra corporeal blood circuits. More particularly, the invention is directed to arterial blood filters used during heart bypass surgery for the removal of particulate matter and gaseous emboli from blood that has been oxygenated and is being returned to the patient.

Blood filters are used for the treatment and filtration of blood for various applications such as cardiopulmonary bypass techniques, blood transfusions, dialysis treatment etc. Arterial blood filters are provided to trap and remove particulate matter and undissolved gaseous emboli from oxygenated blood. Typically, the arterial blood filter is one of the components in an extra corporeal blood circuit in which blood flows from a patient, through a cardiotomy reservoir, an oxygenator and finally into the arterial filter before it is returned to the patient. The arterial blood filter may be the last component of the blood flow circuit through which the blood flows before the blood is returned to the patient, and thus this filter must be durable, reliable and effective in the filtration process.

Arterial blood filters are disposable after a single patient use and must be designed for manufacture, packaging and sterilization at minimal cost. Use of low cost materials and minimization of the amount of materials is critical to the effective manufacture of an arterial filter along with simple, conventional tooling and assembly processes. A small concise design is also a critical factor in packaging costs, efficient sterilization and storage space costs related to the filter. The extra corporeal circuit, including the arterial filter, must be primed with a suitable fluid to remove air from the system prior to the introduction of blood flow; and it is therefore important that the filter have a concise internal volume to minimize priming fluid and priming time in preparation for use.

An example of an early arterial filter having a hollow tubular housing containing a concentric cylindrical filter element is shown in U.S. Pat. No. Re. 32,711 (reissue of U.S. Pat. No. 4,411,783) to Dickens et al. assigned to Shiley Inc. This patent discloses a large diameter cover on the top of the filter element having a symmetrically positioned frusto-conically shaped dome. Blood is introduced tangentially into the upper end of the device and flows over and around the dome then downwardly and through the filter element. The symmetrically positioned dome tends to produce some obstruction to the inlet of blood into the filter, and the flow over the dome tends to create some turbulence and re-circulation with the incoming flow of new blood. The inlet chamber includes a large space for re-circulation and de-bubbling of the blood and results in a relatively large internal volume that requires priming. This early design was considered to be a significant advancement over the prior art at that time, and has been widely used.

Another example of a related prior art arterial filter is described in U.S. Pat. No. 4,919,802 to Katsura, assigned to Terumo Inc. This patent discloses a tubular cylindrical housing with a concentric cylindrical filter element having a symmetrically positioned frusto-conically shaped dome similar to the device of Dickens et al. This patent particularly teaches a horizontally extended tubular blood inlet, adjacent to the cylindrical housing, to introduce blood tangentially into the upper chamber around the side of the symmetrically positioned dome to avoid any obstruction of blood flow by the dome. This patent describes improved performance in de-bubbling and laminar blood flow that does not damage any platelets of the blood cells during the filtering process. The expanded diameter inlet path would seem to require a much larger top cap resulting in more material, a more complex design, complex tooling and assembly for manufacture, and resulting in more external and internal volume and larger packaging and priming requirements.

Another example of a related prior art patent is disclosed in U.S. Pat. No. 5,632,894 to White et al., assigned to Gish Biomedical, Inc. This patent incorporates a tubular housing with a cylindrical filter element having a symmetrically positioned frusto-conically shaped dome similarly to the filter described in the Dickens et al. patent. This patent discloses a tangential tubular blood inlet extended horizontally and adjacent to the side of the housing similarly to the device described in the Katsura patent; and further teaches improves performance by inclining the tubular inlet at an angle, so that the blood is introduced into the filter around the side of the dome and at an upward angle to enhance flow within the filter device. This improvement seems to include the complexity, material and volume requirements as discussed in regard to device in the Katsura patent, plus the additional complexities and costs associated with the inclined inlet and flow path featured in the patent.

In view of the foregoing, it is an object of the present invention to provide a blood filter that has a smooth tangential inlet that is not obstructed by any internal components of the filter.

It is another object to provide a blood filter that provides smooth laminar flow in a downward spiraling vortex that provides efficient separation of any undissolved gases from the blood and does not produce any damage to the blood cells.

It is another object to provide a blood filter that is very compact having minimum external dimensions for efficient packaging and storage and minimal internal dimensions for a low priming volume and efficient blood flow.

SUMMARY OF THE INVENTION

The present invention uniquely improves upon the disclosures and teachings of the prior art in a novel manner to accomplish the desired features and performance of an arterial filter without the complexities and costs associated with those of the prior art.

The foregoing objects are accomplished by an improved compact blood filter device having a central axis suitable for use in a vertical orientation in an extra corporeal blood flow circuit for removing foreign particles and undissolved gases from blood flowing through the device, including a cylindrical body having a circular upper end and a circular lower end forming a filtering chamber therein. Further including, a hollow upper cap having a base diameter closely matched to the diameter of the upper end of the body and attached thereto, forming an inlet chamber therein in communication with the filtering chamber. The upper cap having a vertical gas outlet at the uppermost surface near the center thereof, and having a horizontal tubular inlet therein with the inlet having a horizontal axis and having the outermost edge of the tubular inlet extending tangentially from the outermost wall of the base of the upper cap. The housing further including a substantially flat circular bottom cap having a central tubular blood outlet extending therefrom and having a diameter closely matched to the diameter of the lower end of the body, and attached thereto. The device has a cylindrically shaped filter element having an upper end, a lower end, a filter surface having an outer diameter lesser than the diameter at the lower end of the body, a filter inner surface having a diameter greater than the diameter of the blood outlet, wherein the filter element is positioned coaxially within the filtering chamber of the body and is supported at the lower end thereof on the bottom cap. The inner surface of the filter element is in communication with the outlet chamber, forming an outlet chamber. The filter element is sealed and supported at the upper end and the lower end thereof by conventional means. A principle feature of the present invention is a stepped dome having a circular base with a diameter closely matched to the outer diameter of the filter element and attached to the upper end thereof, and having a hemispherically shaped upper surface extending into the inlet chamber and having a maximum diameter smaller than the diameter of the circular base and having the center of the upper surface offset from the central axis in a direction away from the tubular blood inlet so that the dome does not obstruct the path of blood into and around the blood inlet chamber of the blood filter device. The stepped dome further includes a thin elevated ridge that extends from the base in an upward spiraling manner through about one revolution to the top of the upper surface of said dome to facilitate the removal of undissolved gases and to facilitate the flow of blood flow through the inlet chamber of the device.

The prior art utilizes the tubular housing and concentric cylindrical filter element having a symmetrically shaped dome; however, the upper cap required a horizontally extended (stepped-out) tubular inlet adjacent to the cylindrical housing to introduce the desired blood flow tangentially into the cap and around the side of the symmetrically shaped dome. The present invention provides blood flow tangentially into the cap; however, the blood flow is introduced around the side of the dome by reducing the diameter of the upper dome and offsetting the center of the dome relative to the central axis of the device in a non-symmetrical manner away from the inlet and away from the rear of the cap. The blood flows tangentially into the side of the cap and follows around the inner wall of the cap with no obstruction by the dome and the natural force of gravity and centrifugal force directs the flow of blood into a downwardly widening spiraling path around the inner surface of the cap and then into and around the inner surface of the cylindrical wall into the filtering chamber of the device with smooth laminar flow.

BRIEF DESCRIPTION OF THE DRAWINGS

While the novel features of the invention are set forth in the appended claims, the invention will be better understood along with other features thereof from the following detailed description taken in conjunction with the drawings, in which:

DETAILED DESCRIPTION OF THE INVENTION

Figure 1:
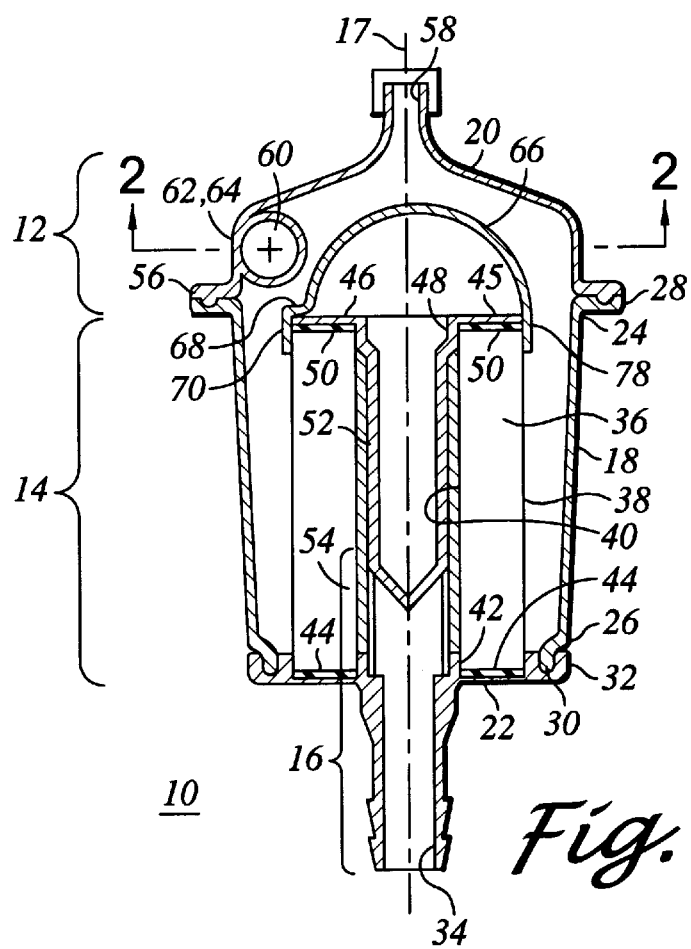
FIG. 1 is a side elevation view in cross section illustrating the components and structure of a preferred embodiment of the blood filter of the present invention.

A preferred embodiment of a blood filter 10 of the present invention is illustrated in FIG. 1. The device will be described in terms of its component parts and structure and further in terms of its function including an inlet chamber 12, a filtering chamber 14 and an outlet chamber 16.

The housing of the blood filter 10 includes a substantially cylindrical body 18, fitted with a hollow substantially frusto-conically shaped upper cap 20 and a substantially flat bottom cap 22.

The body 18 is preferably slightly tapered from top to bottom to facilitate the flow of blood through the device, as discussed later in detail, as well as to facilitate the injection molding process for producing the component. The upper end of the body includes a circumferential flange 28 having a molded groove for bonding the body to the upper cap, and the lower end of the body includes a circumferential flange 30 having a molded tongue for bonding the body to the bottom cap.

The bottom cap 22 is a substantially flat disc having a diameter closely matched with the diameter of the lower end 26 of the body 18, and including a peripheral flange 32 having a groove for engaging the tongue of the flange 30 of the body to facilitate proper alignment and a durable connection of the components. The components are bonded in a fluid-tight sealed manner by conventional adhesive bonding, ultrasonic sealing or RF welding. The bottom cap functions to seal the bottom of the housing and to support a filter element 36 concentrically within the body of the device. The bottom cap further includes an extended tubular blood outlet 34.

The filter element 36 is a conventional filter element that is well known and defined in the prior art (previously incorporated herein by reference) generally comprising a sandwich of micro porous net and fibrous materials that are pressed into a sheet and formed into an accordion of pleats and arranged into a cylindrical shape having a filtering surface 38 and an inner surface 40. The diameter of the filtering surface 38 is less than the diameter of the lower end of the body 26, and the diameter of the inner surface 40 is greater than the diameter of the tubular blood outlet 34. The filter element extends along the length of the cylindrical body 18, and the body and the cylindrical filter surface 38 form the filtering chamber 14 of the device.

The filter element 36 is supported at the lower end by the bottom cap 22. The bottom cap includes a circular interior flange 42 having a diameter corresponding to the diameter of the inner surface 40 of the filter element, and the filter element is supported on the bottom cap between the peripheral flange and the interior flange of the bottom cap. The bottom end of the filter element is sealed within these flanges by casting a suitable hot melt or potting compound seal 44, i.e. polyolefins, polypropylene, polyethylene, ethylene-vinyl-acetate, polyurethane, styrene-butadiene-styrene, silicone rubber or other esastomer. The filter element is supported at the upper end by a filter support 45 comprising an upper disc 46 having a diameter corresponding to the diameter of the filter surface 38 and having a circular flange 48 with a diameter corresponding to the diameter of the inner surface of the filter element extending into the interior of the filter element. The upper end of the filter element is sealed into the upper filter support with a suitable potting compound seal 50. The filter support element 45 further includes a closed-end tube 52 having a diameter smaller than the diameter of the inner surface of the filter element so than blood can readily pass through the filter element, whereby the tube displaces a significant volume within the interior of the filter element to reduce priming volume and priming time and to facilitate blood flow through the device. The volume displacement tube52 includes a set of legs 54 that extend to the bottom cap 22 to further support the filter element. The space within the inner surface of the filter element and the tubular blood outlet of the bottom cap is referred to as the outlet chamber 16. The upper and lower seal construction of the filter element prevents any blood from bypassing to the outlet chamber without passing through the filter element.

The upper cap 20 has a base diameter closely matched to the diameter of the upper end 24 of the body 18 and is fitted to the upper end of the body to complete the housing of the device. The upper cap preferably has a frusto-conical shape, however, it can alternatively have a hemispherical shape or any similarly shaped smooth domed structure to enclose the upper end of the device. The base diameter includes a circumferential flange 56 with a tongue corresponding to fit within the groove of the flange 28 of the body to facilitate proper alignment and a durable connection of the components. The components are bonded in a fluid-tight sealed manner by conventional adhesive bonding, ultrasonic sealing or RF welding. The upper cap includes a vertical gas outlet 58 extending from the uppermost surface, near the center of the cap, to vent the undissolved gases that are separated from the blood during the debubbling and filtration process. The upper cap includes a substantially horizontal tubular inlet 60 extending tangentially from the base of the cap. The internal volume between the upper cap 20 and the upper filter support 46 form the inlet chamber 12 of the device.

The components of the housing including the cylindrical body 18, bottom cap 22, upper cap 20 and upper filter support 46 are preferably formed from transparent polycarbonate material; however, these housing components may be formed of any desired synthetic resigns including polypropylene, polyethylene, styrene-butadiene resin, and methylene-butadiene-styrene resign. These components are preferably transparent to provide easy observation of the contents and filtering process during preparation and in use. The components are illustrated as discrete components that are separately molded and bonded together, however the features and shape of the components can be combined or otherwise produced in a variety of molding choices resulting in the same functional configuration.

Figure 2:
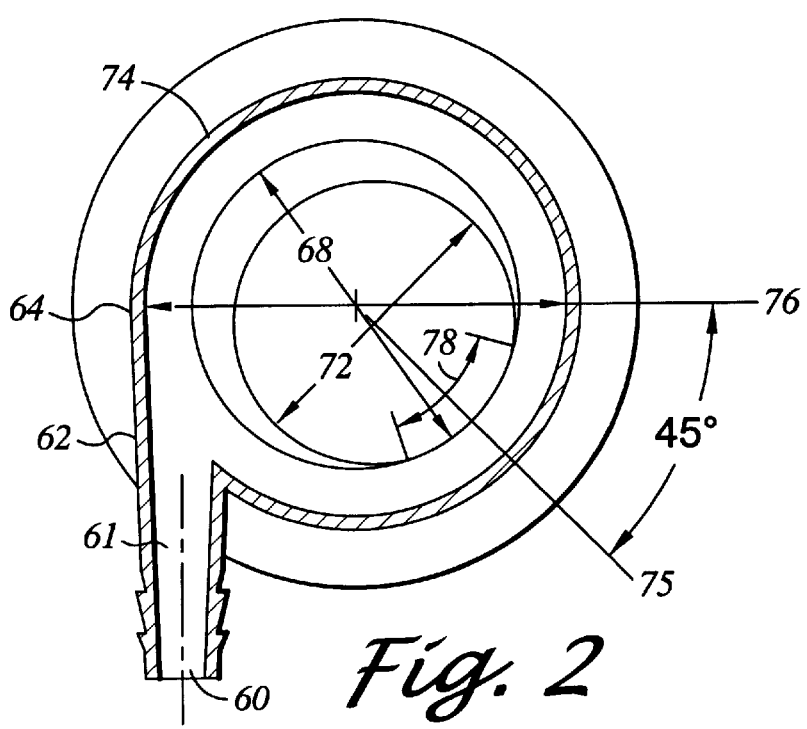
FIG. 2 is a sectional view taken along 2—2 of FIG. 1.

Referring also to FIG. 2, the tubular blood inlet 60 is illustrated, to be uniquely positioned within the base diameter of the upper cap 20, having the outermost edge of the wall 62 of the tubular inlet 62 extending tangentially from the outermost wall 64 of the base of the upper cap. This is considered as a significant design feature of the present invention (which function particularly well with the stepped dome as discussed below) in that the blood from the tubular inlet 62 makes a smooth tangential transition into the inlet chamber and around the inner surface of the cap, which is free from obstructions and turbulence from internal components, to initiate a circular vortex of laminar flow of blood within the device.

Another significant design feature of the present invention is a stepped dome 65 having an upper surface 66 and having a circular base 68 with a diameter closely matched to the outer diameter of the filter surface 38 (and the corresponding filter upper support disc 46); and having the upper surface 66 extending into the inlet chamber and adjacent to the tubular inlet 60. The stepped dome is positioned on the upper end of the filter element and includes a short shirt 70 extending around the top of the filter element 36.

The upper surface 66 of the stepped dome preferably has a circular cross section, and more preferably is hemispherical in shape. However, the upper surface may be frusto-conical in shape or have a variety of combined functionally equivalent contours.

The primary functions of the stepped dome 65 are to displace the unutilized volume within the inlet chamber 12 and to direct flow around the inlet chamber outward and downward into the filtering chamber 14, and further to facilitate the removal of air separated from the blood out through the gas outlet 58. It is important that the dome does not interfere with the inflow of blood from the tubular inlet 60 or with the flow of blood around the upper cap. It was therefore conceived to reduce the maximum diameter of the upper surface of the dome and to offset the upper surface in a direction away from the tubular inlet 60 so that the dome does not obstruct the path of blood into and around the inlet chamber. Incorporation of this unique feature results in a stepped dome having an upper surface with a maximum diameter 72 that is smaller than the diameter of circular base 68. It was further determined that the desired clearance from the inlet and initial flow around the rear wall 74 of the upper cap was maximized by offsetting the center of the upper surface away from the central axis 17 of the device along a line 75 at an angle of about a 45° relative to a line 76 passing through the central axis and perpendicular to the horizontal axis 61 of the tubular inlet 60. The offset distance along the line 75 was further optimized so that a portion of the reduced diameter of the upper surface is aligned to coincide with a portion of the diameter of the base of the dome at 78 to provide a smooth transition of the upper surface 66 with the skirt 70.

Referring also to FIGS. 3–6, there are examples of alternative offset positions of the upper surface 66 of the stepped dome 65 along a line ranging from 0° to 90° relative to a line 76 passing through the central axis of the device and perpendicular to the axis of the blood inlet. These offset positions are considered to be examples of the range of offsets within the teachings of the present invention.

Figure 3:
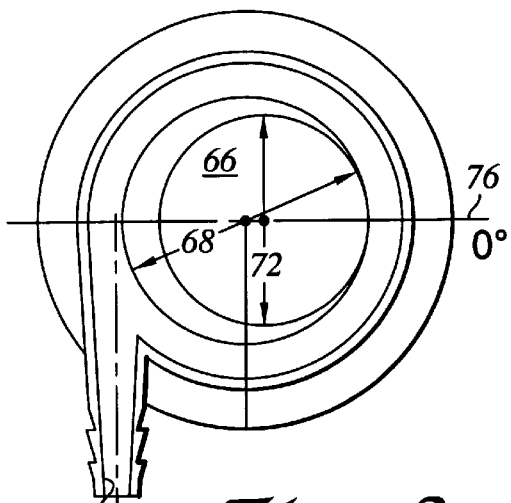
FIG. 3 is a view similar to FIG. 2; illustrating the upper surface of the dome offset relative to the central axis along a line of 0°.

FIG. 3 illustrates an offset of 0° (shifted only to the right of the inlet). This is a very desirable offset configuration providing maximum clearance away from the inlet flow of blood and creating some additional clearance away from the initial flow sector of the rear wall 74.

Figure 4:
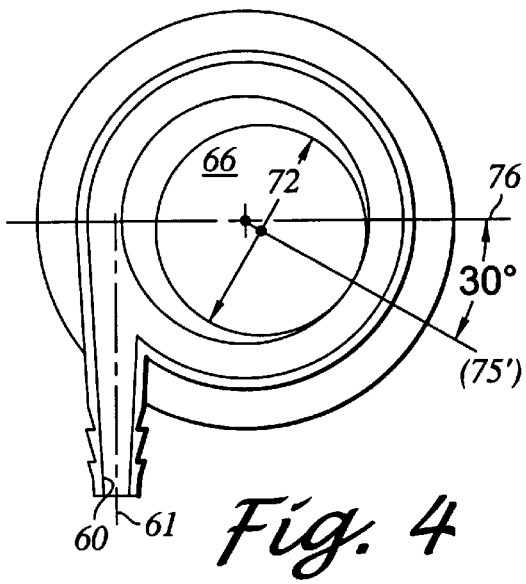
FIG. 4 is a view similar to FIG. 2; illustrating the upper surface of the dome offset relative to the central axis along a line of 30°.
Figure 5:
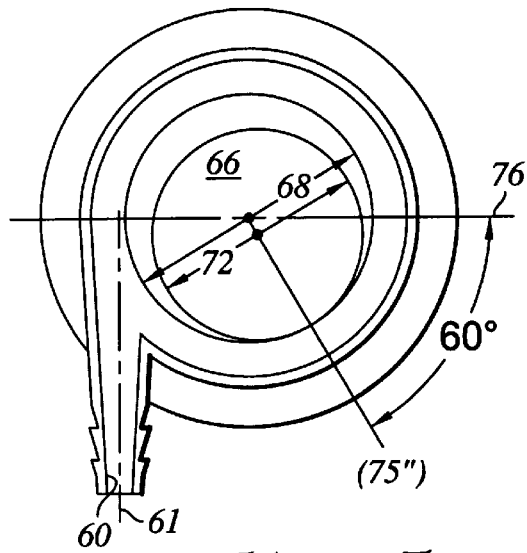
FIG. 5 is a view similar to FIG. 2; illustrating the upper surface of the dome offset relative to the central axis along a line of 60°.

FIG. 4 illustrates an offset oriented along a line at 30°; and FIG. 5 illustrates an offset oriented along a line at 60°. These are also considered to be examples of desirable offsets, and clearly illustrate how the clearances of the upper surface 66 of the dome can be optimized for the desired blood flow around the rear wall 74 of the upper cap.

Figure 6:
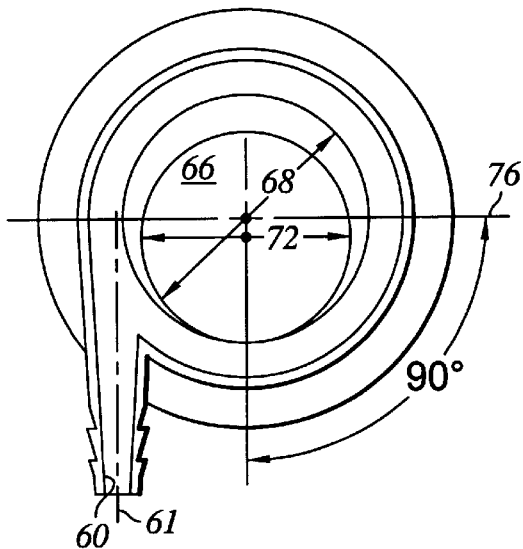
FIG. 6 is a view similar to FIG. 2; illustrating the upper surface of the dome offset relative to the central axis along a line of 90°.

FIG. 6 illustrates an offset oriented along a line at 90° (shifted directly in parallel with the axis of the inlet). This is an extreme example of the offset and illustrates how to create clearance between the upper surface 66 of the dome and the largest peripheral area of the rear wall 74 of the upper cap.

Figure 7:
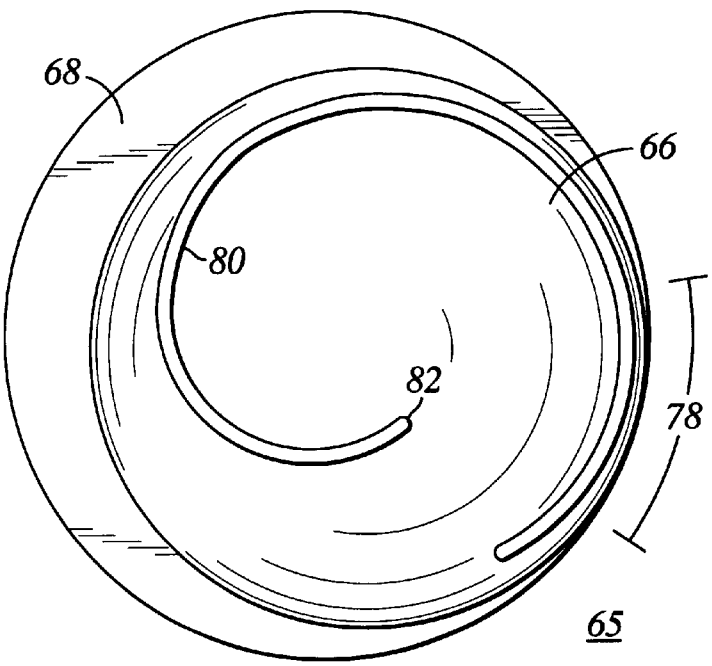
FIG. 7 is an enlarged top plan view of the stepped dome illustrating the upward spiraling ridge of the present invention.
Figure 8:
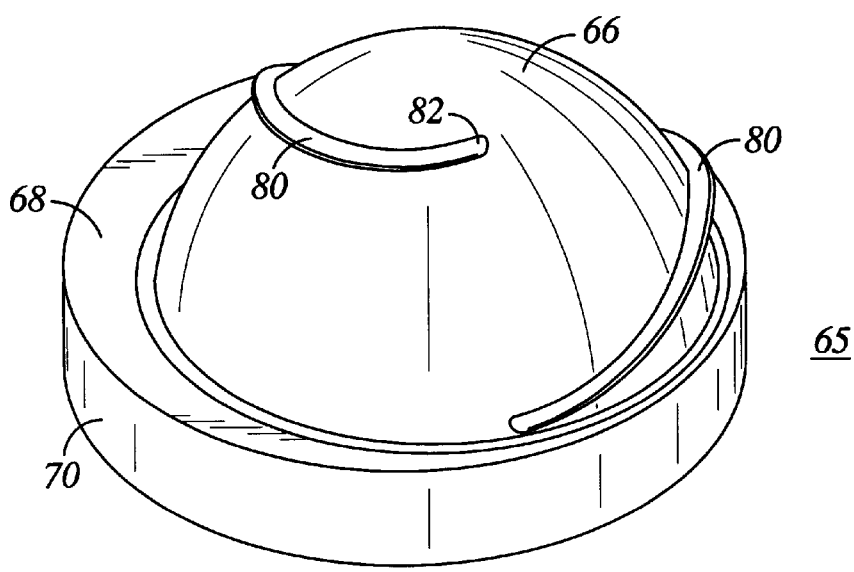
FIG. 8 is an enlarged top front perspective view of the stepped dome of FIG. 7.

FIGS. 7 and 8 particularly illustrate another feature of the present invention in which the upper surface 66 of the stepped dome 65 further includes a thin elevated ridge 80 that extends from the base 68 in an upward spiraling manner through about one revolution to a point 82 near the top of the upper surface of the dome. The ridge preferably has a semicircular cross section about 0.06 inches wide and elevated to a height of about 0.03 inches above the surface of the dome. In the example of the embodiment (as illustrated in FIG. 2) the blood inlet 60 is positioned on the left side and the resulting blood flow is in a clockwise direction. The spiral ridge 80 is preferably oriented to incline in a counterclockwise upward spiral (clockwise downward spiral) to advantageously direct any blood flow that may engage the upper surface of the stepped dome to be directed downwardly by the ridge into the filtering chamber. The ridge further provides a path for the gases from the base of the stepped dome along the upper dome surface to facilitate venting through outlet 58. This feature tends to further preclude re-circulation of blood into the inlet flow of new blood, which would otherwise tend to create turbulence of the blood flow through the inlet chamber.

Alternatively, the ridge (80) may be oriented to incline upwardly in a clockwise spiral to facilitate the venting of the gases from the inlet chamber. It was found that the air bubbles that migrate by centrifugal effect toward the center of the inlet chamber are naturally influenced by the blood flow path and the clockwise inclined ridge 80 upwardly to facilitate venting of the gas through outlet 58.

Figure 9:
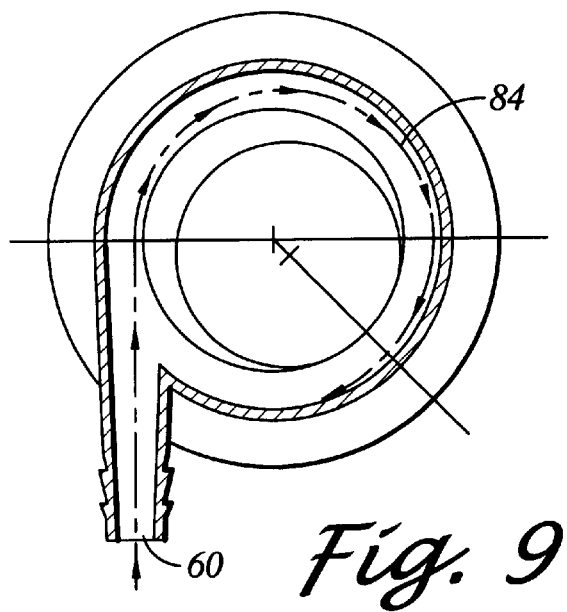
FIG. 9 is a view similar to FIG. 2; illustrating the blood path flow through the inlet chamber of the device.
Figure 10:
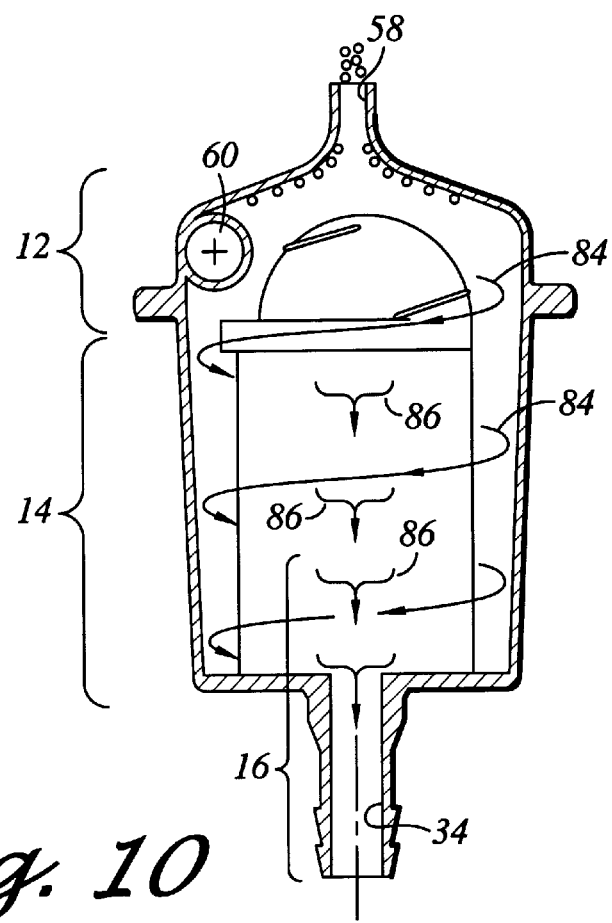
FIG. 10 is a front elevation view partially sectioned to illustrate the blood path flow through the device.

Referring now to FIGS. 1, 9 and 10, the smooth flow of blood into and through the blood filter device 10 of the present invention is described in more detail. The oxygenated blood is pumped through the extra corporeal circuit to the blood inlet 60 of the arterial blood filter. The blood is introduced tangentially within the upper cap 20 under pressure and having velocity and inertia, and is directed by the cylindrical inner surface of the upper cap into a circular path around the interior of the upper cap. The internal surfaces and components of the present design present no obstruction to the flow and create no turbulence or cavitation of the flow. The blood flow is influenced primarily by the cylindrical walls of the upper cap and the downward force of gravity resulting in a smooth spiraling vortex path through the inlet chamber 12. Tests indicate that after one revolution around the device, the level of the flow of blood is sufficiently lowered so that the blood path passes below the blood inlet 60 and therefore does not interfere with the flow of new blood. A typical blood flow pattern is illustrated by the arrows 84 indicating the downward spiraling vortex path through the device. The smooth internal configuration and natural flow path are believed to result in the highly desirable laminar blood flow through the device that does not damage cells and platelets. Tests also indicate very little pressure drop through the device.

The undissolved gases and air bubbles that are present in the blood are removed by virtue of a centrifugal effect that bubbles, with a small mass entrained in a swirl flow, and will separate and be forced to the interior of the flow. The separated bubbles will float and collect at the axial center of the device and are allowed to escape through the gas outlet 58 at the uppermost point near the center of the upper cap. The remaining gas bubbles are further separated due to natural pressure and movement of the blood around the filtering chamber. The slightly tapered wall of the body 18 tends to narrow the space near the lower end of the filter chamber creating some additional pressure which also tends to release entrained gas bubbles from the blood and allow them to be vented through the gas outlet. The undissolved gases that are not separated by centrifugal force and natural fluid pressure are separated at the filter surface 38 of the filter element 36 and migrate upward and eventually are vented at the upper gas outlet for efficient reliable debubbling of the gases from the blood.

The blood continues in a downwardly spiraling vortex manner through the filtering chamber 14 where the blood passes through the filter surface 38 of the filter element 36. Any foreign matter is filtered from the blood and the blood passes through the inner surface 40 of the filter and into the outlet chamber 16 as indicated by arrows 86. The debubbled and filtered blood is discharged through the blood outlet 34 and returned through suitable tubing of the circuit to the patient.

The present invention discloses exemplary embodiments of an improved arterial blood filter that has a smooth tangential inlet that is not obstructed by any internal components of the filter. The filter of the present invention provides efficient separation of any undissolved gases from the blood and provides smooth laminar flow in a downward spiraling vortex through the device and thus does not produce any damage to platelets or blood cells. The device is very inexpensive to manufacture and very compact having minimum external dimensions for efficient packaging and storage and minimal internal dimensions for a low priming volume and efficient blood flow.

While specific embodiments and examples of the present invention have been illustrated and described herein, it is realized that modifications and changes will occur to those skilled in the art. It is therefore to be understood that the appended claims are intended to cover all such modifications and changes as fall within the spirit and scope of the invention.

What is claimed is:

1. A blood filter device having a central longitudinal axis suitable for use in a vertical orientation in an extra corporeal blood flow circuit for removing foreign particles and undissolved gases from blood flowing through the device, comprising:

a substantially cylindrical body having a circular upper end and a circular lower end forming a filtering chamber therein;

a hollow substantially frusto-conically shaped upper cap having a base diameter closely matched to the diameter of the upper end of said body and attached thereto, forming an inlet chamber therein in communication with the filtering chamber;

said upper cap having a vertical gas outlet at the uppermost surface near the center thereof, and having a horizontal tubular inlet therein with the inlet having a horizontal axis and having the outermost wall of the tubular inlet extending tangentially from the outermost wall of the base of said upper cap;

a substantially flat circular bottom cap having a central tubular blood outlet extending therefrom and having a diameter closely matched to the diameter of the lower end of said body, and attached thereto;

a cylindrically shaped filter element having an upper end, a lower end, a filter surface having an outer diameter lesser than the diameter at the lower end of said body, a filter inner surface having a diameter greater than the diameter of the tubular blood outlet, wherein said filter element is positioned coaxially within the filtering chamber of said body and supported at the lower end thereof on said bottom cap, with the inner surface thereof in communication with the outlet chamber, forming an outlet chamber therein;

means for sealing and supporting the upper end of said filter element;

means for sealing the lower end of said filter element;

a stepped dome having a circular base with a diameter closely matched to the outer diameter of said filter element and attached to the upper end thereof, and having an upper surface with a substantially circular cross-section extending into the inlet chamber having a maximum diameter smaller than the diameter of the circular base and having the center of the upper surface offset from the central axis in a direction away from the tubular blood inlet so that the dome does not obstruct the path of blood into and around the blood inlet chamber of the blood filter device.

2. The blood filter device of claim 1 wherein said stepped dome is further offset from the central axis in a direction away from the rearward wall of the cap so that the dome does not obstruct the path of blood into and around the blood inlet chamber of the blood filter device.

3. The blood filter device of claim 1 wherein said stepped dome is offset from the central axis in a direction away from the tubular blood inlet and in a direction away from the rearward wall of said upper cap along a line ranging from 0° to 90° relative to a line passing through the central axis and perpendicular to the horizontal axis of the blood inlet.

4. The blood filter of claim 3 wherein the upper surface of said stepped dome is frusto-conically shaped.

5. The blood filter of claim 3 wherein the upper surface of said stepped dome is substantially hemispherically shaped.

6. The blood filter device of claim 3 wherein a portion of the diameter of the upper surface coincides with a portion of the diameter of the base of said stepped dome.

7. The blood filter of claim 3 wherein the offset is along a line at an angle of about 45°.

8. The blood filter of claim 3 wherein the offset is along a line at an angle of about 0°.

9. The blood filter of claim 3 wherein the offset is along a line at an angle of about 30°.

10. The blood filter of claim 3 wherein the offset is along a line at an angle of about 60°.

11. The blood filter of claim 3 wherein the offset is along a line at an angle of about 90°.

12. The blood filter of claim 3 wherein the upper surface of said stepped dome further includes an elevated ridge that extends from the base in an upward spiraling manner through about one revolution to the top of the upper surface of said dome.

13. The blood filter of claim 12 wherein the elevated ridge extends upward in a spiraling manner in a counter-clockwise direction.

14. The blood filter of claim 13 wherein the elevated ridge extends upward in a spiraling manner in a clockwise direction.

15. A blood filter device having a central longitudinal axis suitable for use in a vertical orientation in an extra corporeal blood flow circuit for removing foreign particles and undissolved gases from blood flowing through the device, comprising:

a substantially cylindrical body having a circular upper end and a circular lower end forming a filtering chamber therein;

a hollow substantially frusto-conically shaped upper cap having a base diameter closely matched to the diameter of the upper end of said body and attached thereto, forming an inlet chamber therein in communication with the filtering chamber;

said upper cap having a vertical gas outlet at the uppermost surface near the center thereof, and having a horizontal tubular inlet therein with the inlet having a horizontal axis and having the outermost edge of the wall of the tubular inlet extending tangentially from the outermost wall of the base of said upper cap;

a substantially flat circular bottom cap having a central tubular blood outlet extending therefrom and having a diameter closely matched to the diameter of the lower end of said body, and attached thereto;

a cylindrically shaped filter element having an upper end, a lower end, a filter surface having an outer diameter lesser than the diameter at the lower end of said body, a filter inner surface having a diameter greater than the diameter of the blood outlet, wherein said filter element is positioned coaxially within the filtering chamber of said body and supported at the lower end thereof on said bottom cap, with the inner surface thereof in communication with the outlet chamber, forming an outlet chamber therein;

means for sealing and supporting the upper end of said filter element;

means for sealing the lower end of said filter element;

a stepped dome having a circular base with a diameter closely matched to the outer diameter of said filter element and attached to the upper end thereof, and having a substantially hemispherically shaped upper surface extending into the inlet chamber having a maximum diameter smaller than the diameter of the circular base and having the center of the upper surface offset from the central axis in a direction away from the tubular blood inlet and away from the rear wall of said upper cap along a line at an angle of about 45° relative to a line passing through the central axis and perpendicular to the horizontal axis of the blood inlet, so that the dome does not obstruct the path of blood into and around the blood inlet chamber of the blood filter device;

said stepped dome further including an elevated ridge that extends from the base in an upward spiraling manner through about one revolution to the top of the upper surface of said dome to facilitate the removal of undissolved gases and to facilitate the flow of blood flow through the inlet chamber of the device.

* * * * *